US012383718B2

(12) United States Patent
Weiss

(10) Patent No.: US 12,383,718 B2
(45) Date of Patent: Aug. 12, 2025

(54) TUBE CONNECTOR FOR MEDICAL TUBE LINES

(71) Applicant: B. Braun Melsungen AG, Melsungen (DE)

(72) Inventor: André Weiss, Guxhagen (DE)

(73) Assignee: B. Braun Melsungen AG, Melsungen (DE)

( * ) Notice: Subject to any disclaimer, the term of this patent is extended or adjusted under 35 U.S.C. 154(b) by 7 days.

(21) Appl. No.: 18/566,285

(22) PCT Filed: Jun. 1, 2022

(86) PCT No.: PCT/EP2022/064924
§ 371 (c)(1),
(2) Date: Dec. 1, 2023

(87) PCT Pub. No.: WO2022/253900
PCT Pub. Date: Dec. 8, 2022

(65) Prior Publication Data
US 2024/0245897 A1    Jul. 25, 2024

(30) Foreign Application Priority Data
Jun. 2, 2021   (DE) .................. 10 2021 205 602.4

(51) Int. Cl.
*A61M 39/10*    (2006.01)
*F16L 33/30*    (2006.01)

(52) U.S. Cl.
CPC ............ *A61M 39/10* (2013.01); *F16L 33/30* (2013.01)

(58) Field of Classification Search
CPC .... A61M 39/10; A61M 39/146; A61M 39/12; F16L 33/32; F16L 33/30
See application file for complete search history.

(56) References Cited

U.S. PATENT DOCUMENTS

| 287,414 A | 10/1883 | Brown |
| 589,216 A * | 8/1897 | McKee ................. F16L 33/30 |
| | | 285/259 |

(Continued)

FOREIGN PATENT DOCUMENTS

| EP | 0645161 B1 | 2/2002 |
| KR | 1020190118046 A | 10/2019 |

OTHER PUBLICATIONS

Search Report received in International Application No. PCT/EP2022/064924 dated Sep. 5, 2022, with translation, 4 pages.

*Primary Examiner* — David Bochna
(74) *Attorney, Agent, or Firm* — Christopher A. Rothe; CM Law

(57) ABSTRACT

A tube connector usable with medical tube lines includes a body having a first end, a second end, a first mating section, and a second mating section. The first mating section is configured for insertion into a first tube end of a first medical tube line. The second mating section is configured for mating with a second tube end of a second medical tube line. A connecting lumen extends through the body between the first end and second end. The connecting lumen forms a fluid connection between the first medical tube line and second medical tube line when the first mating section mates with the first tube end and the second mating section mates with the second tube end. The body has at least one blade section and a cutting edge. The first tube end is slitable by the cutting edge upon insertion of the first mating section.

16 Claims, 6 Drawing Sheets

(56) References Cited

U.S. PATENT DOCUMENTS

| | | | | |
|---|---|---|---|---|
| 2,731,279 | A * | 1/1956 | Main, Jr. | F16L 33/16 |
| | | | | 285/259 |
| 3,423,109 | A * | 1/1969 | New | F16L 33/2073 |
| | | | | 285/256 |
| 4,405,969 | A * | 9/1983 | Swavely | F16L 33/2071 |
| | | | | 174/47 |
| 5,487,571 | A * | 1/1996 | Robertson | F16L 33/30 |
| | | | | 285/259 |
| 6,524,304 | B1 * | 2/2003 | Picou | A61M 39/10 |
| | | | | 604/534 |
| 7,914,049 | B2 | 3/2011 | Vinci | |
| 8,783,732 | B2 * | 7/2014 | Smith | F16L 33/01 |
| | | | | 285/259 |
| 8,943,668 | B2 * | 2/2015 | Menor | F16L 33/2073 |
| | | | | 285/256 |
| 11,517,732 | B2 * | 12/2022 | Ziebol | A61M 39/162 |
| 2012/0248759 | A1 * | 10/2012 | Feith | F16L 33/30 |
| | | | | 137/15.01 |
| 2015/0352342 | A1 | 12/2015 | Lesch, Jr. et al. | |
| 2016/0327194 | A1 | 11/2016 | Wells | |

* cited by examiner

TUBE CONNECTOR FOR MEDICAL TUBE LINES

CROSS-REFERENCE TO RELATED APPLICATIONS

This application is the United States national phase entry of International Application No. PCT/EP2022/064924, filed on Jun. 1, 2022, and claims priority to German Application No. 10 2021 205 602.4, filed on Jun. 2, 2021. The contents of International Application No. PCT/EP2022/064924 and German Application No. 10 2021 205 602.4 are incorporated by reference herein in their entireties.

FIELD

The invention relates to a tube connector for medical tube lines, comprising a body having a first end and a second end, a male first mating section which is arranged at the first end and which is configured for axial insertion into a tube end of a first medical tube line along a first mating axis, a male or female second mating section which is arranged at the second end and which is configured for axial mating with a tube end of a second medical tube line along a second mating axis, and comprising a connecting lumen which is elongate between the first end and the second end through the body and which, when the two mating sections are mated with the respective tube end, forms a fluid connection between the two medical tube lines.

BACKGROUND

Such tube connectors are generally known in the field of medical technology and are intended for connection of medical tube lines.

For example, EP 0 645 161 B1 discloses a tube connector for medical applications. The known tube connector comprises a body which is made of a rubber-elastic material and which has opposite mating sections in the longitudinal direction. There, the mating sections are both in the form of female mating sections and, in this respect, configured for fitting onto a tube end of the tube lines to be connected. A connecting lumen is elongate between the mating sections.

SUMMARY

It is an object of the invention to provide a tube connector of the type mentioned at the beginning that avoids excessive mechanical stress on the tube ends and at the same time allows particularly simple connection of the medical tube lines.

This object is achieved by the body having at least one blade section which is assigned to the first mating section and has a cutting edge oriented in the direction of the first mating axis, by means of which the tube end of the first medical tube line is axially slitable upon insertion of the first mating section. What is achieved by the invention is that the tube end of the first medical tube line is simultaneously axially slit upon insertion of the first mating section. Present for this purpose is the blade section, more precisely the cutting edge thereof. The axial slitting of the tube end avoids overstretching under the action of the first mating section. The inventor has recognized that such overstretching in the radial direction and/or circumferential direction of the tube end can lead in particular to leaks and other problems. Moreover, the axial slitting allows simple positioning of the tube connector in the longitudinal direction of the first medical tube line. To this end, the tube connector according to the invention is advanced further axially along the first medical tube line after insertion into the tube end. During this advance, the first medical tube line, more precisely the tube casing thereof, is longitudinally slit proceeding from its tube end under the action of the cutting edge. Once a desired longitudinal position of the tube connector—and hence an effective length of the first medical tube line—has been reached, the section which is axially protruding and has been slit can be removed. Since excessive mechanical stress is avoided and since it is possible to position the tube connector on the first medical tube line in the axial direction in a simple manner, there are also significant advantages with respect to the production of medical tube arrangements. Such a medical tube arrangement includes, for example, a catheter arrangement, in particular a central venous catheter arrangement having one or more lumens. The inventor has recognized that the production of central venous catheter arrangements can be significantly simplified using the tube connector according to the invention. The first mating section is in the form of a male mating section and thus configured for axial insertion into the tube end of the first medical tube line. The tube end of the first medical tube line is also referred to below as first tube end. In an inserted state, an outer contour of the first mating section interacts with an inner contour of the first tube end. The outer contour is matched to the inner contour of the first tube end dimensionally and/or in terms of its shape. The second mating section is in the form of a male or female mating section. If the second mating section is in the form of a male mating section, what has been stated above in relation to the first mating section applies mutatis mutandis. If the second mating section is in the form of a female mating section, it is configured for fitting onto the tube end of the second medical tube line. The tube end of the second medical tube line is also referred to below as second tube end. When the female second mating section is fitted, the inner contour thereof interacts with an outer contour of the second tube end. The inner contour of the female second mating section is matched to the outer contour of the second tube end dimensionally and/or in terms of its shape. In the mated state, a first mated connection is formed between the first mating section and the first tube end. A second mated connection is accordingly formed between the second mating section and the second tube end. The first and the second mated connections are both preferably fluid-tight. To this end, the two mating sections are respectively matched to the respective tube end dimensionally and/or in terms of their shape. The first mated connection and/or the second mated connection is/are preferably separable. Alternatively, a non-separable design of the first and/or the second mated connection is conceivable. In one embodiment, the first and/or the second mating section are integrally formed on the body. In other embodiments, at least one of the mating sections is manufactured as a separate component and then joined together with the body and/or the further mating section. In a mated state, the first mating axis coincides with a longitudinal axis of the first tube end. In a mated state, the second mating axis coincides with a longitudinal axis of the second tube end. Alternatively or additionally, the first mating axis can coincide with a longitudinal axis of a lumen of the first medical tube line. Alternatively or additionally, the second mating axis can coincide with a longitudinal axis of a lumen of the second medical tube line. The first mating axis and the second mating axis can in principle be oriented relative to each other as desired. In different embodiments, the first mating axis and the second mating axis are oriented parallel, coaxially, angled and/or obliquely in some other way to each other. The connecting lumen can be elongate between the first end and the second end in a straight, angled, cranked and/or curved manner. One end of the connecting lumen has a first opening assigned to the first mating section and the other end has a second opening assigned to the second mating section. The blade section is arranged between the first end and the second end of the body. Preferably, one end of the blade section is connected to the first mating section and/or the second mating section and the other end has the cutting edge. In one embodiment, the cutting edge is elongate in a straight line, in particular continuously, between a first edge end and a second edge end. In other embodiments, the cutting edge is elongate in a curved manner between the first edge end and the second edge end. The cutting edge can be in particular smooth, undulating and/or serrated. The second medical tube line is preferably a catheter supply line of a central venous catheter. The first medical tube line is preferably a catheter tube of the central venous catheter. Preferably, the central venous catheter, more precisely the catheter tube thereof, has multiple lumens for fluid connection to one catheter supply line each.

In one embodiment, the cutting edge is configured for cutting through a tube casing of the first medical tube line, so that the tube connector, when the first mating section is inserted into the first tube line, can be positioned along the first medical tube line while cutting through the tube casing by means of the cutting edge. Consequently, the cutting edge is not configured merely for making a radial surface scratch or partially penetrating cut, but for completely cutting through the tube casing instead. Preferably, the cutting edge is matched dimensionally to the tube casing to be cut through, in particular the wall thickness thereof, and so said tube casing can be cut through completely.

In one embodiment, the blade section protrudes outwardly from the first mating section in the radial direction. This allows a particularly simple construction of the tube connector. Radial direction means the radial direction of the first mating section. The radial direction is oriented orthogonally to the first mating axis. Alternatively or additionally, the blade section can protrude in the axial direction from a rear end face of the second mating section that faces away from the second end. Axial in this context means an orientation oriented along the first mating axis and/or the second mating axis.

In one embodiment, the cutting edge is elongate at an inclination relative to the first mating axis. The longitudinal inclination of the cutting edge allows particularly smooth slitting of the first tube end. As a consequence of the longitudinal inclination, the cutting edge upon insertion of the first mating section does not hit the first tube end abruptly over the entire length of said cutting edge. Instead, the longitudinally inclined cutting edge enters the material of the first tube end to be cut through gradually over the length of said cutting edge.

In one embodiment, the cutting edge has a first edge end positioned nearer to the first end and a second edge end positioned nearer to the second end, the first edge end being recessed axially in the direction of the second end by an axial distance along the first mating axis relative to an end face of the first mating section. Said axial distance ensures that the first tube end is not slit over the entire length of the first mating section. This could lead to the first mating section not being held sufficiently firmly in the first tube end. Instead, owing to the axial distance, the first tube end upon complete insertion of the first mating section is in any case not slit over the length of the axial distance. The first edge end is positioned nearer to the first end of the body than the second edge end. In this respect, the first edge end points in the direction of the material of the first tube end to be cut through. The end face of the first mating section preferably simultaneously forms an end face of the body.

In one embodiment, the axial distance is between 30% and 70%, preferably between 40% and 60%, particularly preferably 50%, of a total length of the first mating section. Said value ranges have been found to be advantageous.

In one embodiment, the first edge end is flush with an outer contour of the first mating section and the second edge end is flush with an outer contour of the second mating section. This embodiment of the invention is advantageous as regards construction and function. Firstly, excessive mechanical stress can be avoided owing to the flush-mounted edge ends. This counteracts damage to the cutting edge. Secondly, the flush arrangement of the first edge end entails the tube casing of the first tube line being cut through continuously in a radial direction proceeding from its internal circumference. As a result, the tube connector can be advanced along the first medical tube line particularly smoothly for the purpose of assembly.

In one embodiment, the first mating section has a first outer conical surface and/or the second mating section has a second outer conical surface or an inner conical surface. The conical design of the outer contour of the first mating section and/or the second mating section can compensate for dimensional deviations of the tube ends to be connected. The cross-section of the first outer conical surface is matched to the inner contour of the first tube end. If the first tube end has a circular-cylindrical inner contour, more precisely a circular-cylindrical lumen, the first outer conical surface has a complementary circular cross-section. Multilumen catheter tubes often have semicircular or crescent lumens. Accordingly, in other embodiments, the cross-section of the first outer conical surface is matched thereto semicircularly or crescently. If the second mating section is in the form of a male mating section, it has the second outer conical surface. If the second mating section is the form of a female mating section, it has the inner conical surface.

In one embodiment, the first mating axis and the second mating axis are parallel oriented and are axially spaced by a radial distance. In this respect, there can also be said to be a radial axis offset between the first mating axis and the second mating axis.

In one embodiment, the connecting lumen is oblique in relation to the two mating axes and is elongate in a continuous straight line along a lumen axis. The continuously straight longitudinal extent of the connecting lumen offers advantages especially in manufacture.

In one embodiment, the first mating axis and the second mating axis are elongate at an inclination to each other. Accordingly, the body is angled and/or cranked.

In one embodiment, the connecting lumen is angled at least once, one section of the connecting lumen being elongate coaxially to the first mating axis and one section of the connecting lumen being elongate coaxially to the second mating axis. The connecting lumen therefore has at least one angular section, curved section and/or kink. In other embodiments, the connecting lumen is doubly angled or multiply angled.

Since the two mating axes are oriented with a radial axis offset and/or at an inclination to each other, this allows simple adaptation to predetermined angles, or angles to be achieved, between the first medical tube line and the second medical tube line.

In one embodiment, the body is made of a plastics material in one piece. This allows simple and cost-effective production in large quantities.

The invention further relates to a catheter arrangement, in particular central venous catheter arrangement, comprising at least one catheter supply line, a catheter tube, and comprising a tube connector as described above, the catheter supply line and the catheter tube being connected to each other by means of the tube connector, and there being present a fixing section by means of which the connection between the catheter supply line and the catheter tube is fixed. The tube connector establishes a connection between the catheter supply line and the catheter tube that is separable on its own. The fixing section brings about a fixation of this connection that is separable on its own. The tube connector primarily acts as an assembly aid and, prior to the attachment of the fixing section, one end is attached to the catheter supply line and the other end is attached to the catheter tube. The fixing section prevents separation of the connection established by means of the tube connector. The fixing section is different in different embodiments and can be, for example, an additional adhesive bond, an overmold, preferably a plastics overmold, or an encapsulation, preferably with a potting compound.

In one embodiment, the fixing section is formed by a plastics overmold, the plastics overmold completely sheathing the tube connector. This is a particularly preferred embodiment of the invention. The plastics overmold on its own can in principle be defect-prone. For example, voids in the plastics overmold can lead to undesirable leaks, cross-connections or the like. The use of the tube connector as a kind of assembly aid for the actual joining process by means of the plastics overmold prevents said defects of the plastics overmold from taking effect in a disadvantageous manner.

BRIEF DESCRIPTION OF THE DRAWINGS

Further advantages and features of the invention will become apparent from the following description of preferred exemplary embodiments of the invention which are illustrated with the aid of the drawings.

DETAILED DESCRIPTION

Figure 1:
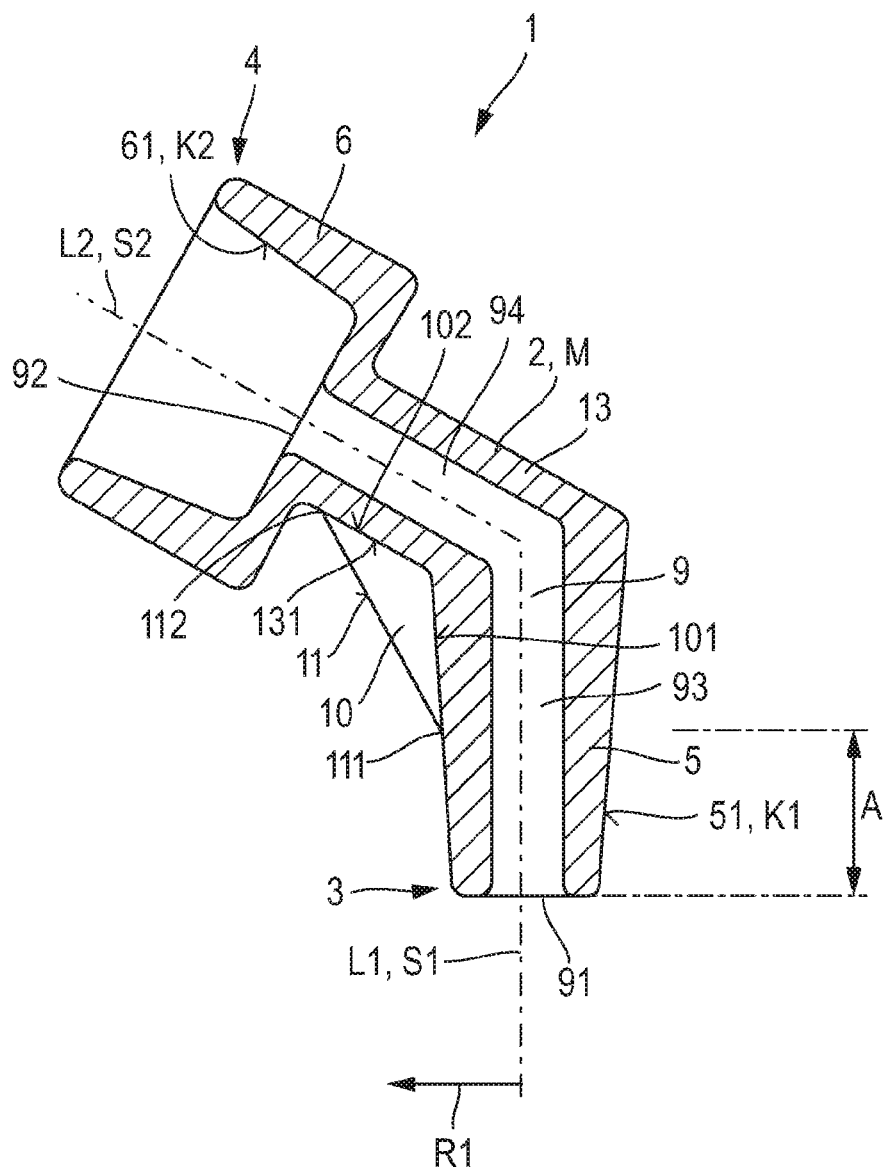
FIG. 1 shows a schematic longitudinal section of one embodiment of a tube connector according to the invention for medical tube lines.
Figure 2:
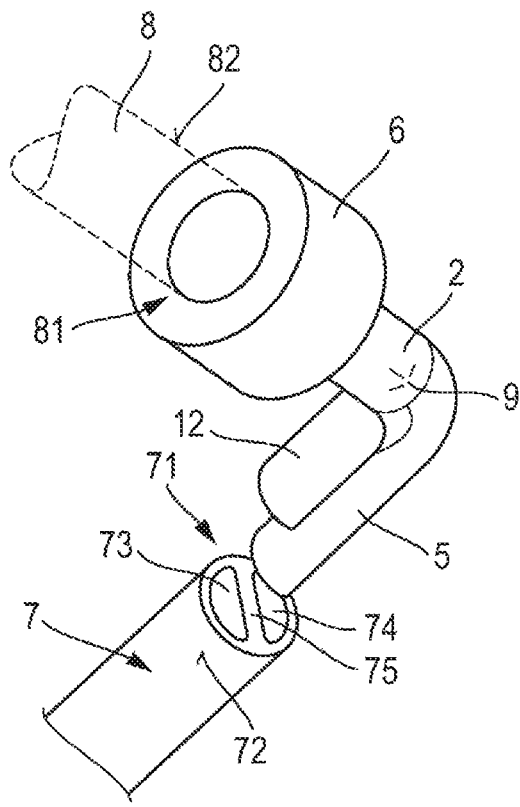
FIG. 2 shows a partially cropped perspective view of a first configuration of an arrangement comprising the tube connector as per FIG. 1 and a first medical tube line and a second medical tube line.

According to FIG. 1, a tube connector 1 is intended for connection of medical tube lines 7, 8 (FIG. 2, 3). The tube connector 1 can also be referred to as an assembly aid.

The tube connector 1 comprises a body 2 having a first end 3 and a second end 4. Arranged at the first end 3 is a first mating section 5, and arranged at the second end 4 is a second mating section 6. The first mating section 5 and the second mating section 6 are both configured for mating with one of the two medical tube lines 7, 8.

The first mating section 5 is in the form of a male mating section and, in this respect, configured for axial insertion into a tube end 71 of the medical tube line 7. The medical tube line 7 is also referred to below as first tube line. Accordingly, the tube end 71 thereof is referred to as first tube end. The axial insertion is effected along a first mating axis S1. In the present case, the first mating axis S1 simultaneously forms a longitudinal axis L1 of the first mating section 5, which is also referred to below as first longitudinal axis L1.

The second mating section 6 can be, in principle, in the form of a male or female mating section. In the embodiment shown, the second mating section 6 is in the form of a female mating section and, in this respect, configured for axial fitting onto a tube end 81 of the medical tube line 8. The medical tube line 8 is also referred to below as second medical tube line. The tube end 81 is therefore also referred to as second tube end. The mating with the second tube end 81 is effected along a second mating axis S2. In the present case, it simultaneously forms a second longitudinal axis L2 assigned to the second mating section 6.

Figure 3:
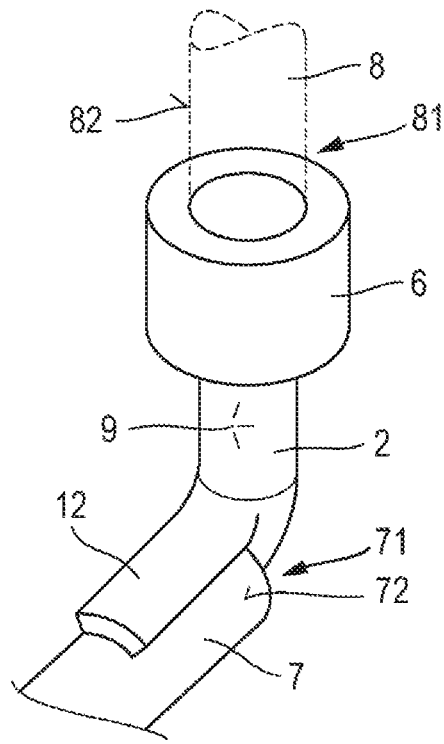
FIG. 3 shows a further configuration of the arrangement as per FIG. 2.

Furthermore, the tube connector 1 comprises a connecting lumen 9 which is elongate through the body 2. The connecting lumen 9 is elongate between the first end 3 and the second end 4 through the body 2. At the same time, one end of the lumen 9 has a first opening 91 and the other end has a second opening 92. The first opening 91 is assigned to the first end 3 and hence to the first mating section 5. The second opening 92 is assigned to the second end 4 and hence to the second mating section 6. When the two mating sections 5, 6 are mated with the respective tube end 71, 81, the lumen 9 forms a fluid connection between the two medical tube lines 7, 8 (FIG. 3).

Furthermore, the tube connector 1 has at least one blade section 10 which is assigned to the first mating section 5 and has a cutting edge 11. The cutting edge 11 is configured for axial slitting of the first tube end 71. In particular, the cutting edge 11 is configured for slitting and/or cutting through the tube casing 72 of the first tube line 7. The cutting edge 11 is oriented in the direction of the first mating axis S1, and so the tube casing 72 is simultaneously axially slit upon insertion of the first mating section 5 into the first tube end 71. Firstly, this can counteract overstretching of the first tube end 71 in the circumferential direction. Secondly, the tube connector 1, when the first mating section 5 is inserted, can be positioned in a simple manner along the first tube line 7 while cutting through the tube casing 72 by means of the cutting edge 11.

The functioning and use of the tube connector 1 can be described as follows:

For fluid connection of the first tube line 7 to the second tube line 8, the second tube end 81 is first inserted into the second mating section 6 axially along the second mating axis S2. This results in the state which can be seen from FIG. 2. Proceeding from this state, the first mating section 5 is inserted axially along the first mating axis S1 into the first tube end 71. Owing to the action of the blade section 10, more precisely the cutting edge 11 thereof, the tube casing 72 is slit axially in this connection in the region of the first tube end 71. This results in the configuration shown by means of FIG. 3. In this configuration, the first medical tube line 7 and the second medical tube line 8 are fluidically connected to each other via the connecting lumen 9. The mated connections formed between the mating sections 5, 6 and the respective tube end 71, 81 are fluid-tight.

After the first tube line 7 and the second tube line 8 have been connected to each other in the manner described above, the connection can be fixed. Conventional techniques, for example bonding, potting and overmolding, are suitable for this purpose. Moreover, fixation by means of tube clamps or the like is conceivable. Fixation prevents separation of the connection. If such fixation is not available, the connection brought about by means of the tube connector 1 may become separated. In other words: the tube connector 1, on its own, merely brings about a separable connection of the tube lines 7, 8.

In the embodiment shown, the tube connector 1 also has a leg section 12. It is shown by means of FIGS. 2 and 3 and is hidden in FIG. 1 for drawing-related reasons. The leg section 12, when there is mating with the first medical tube line 7, rests radially on the tube casing 72 thereof, and it is elongate approximately parallel to the first mating section 5. The leg section 12 covers the blade section 10 and the cutting edge 11 thereof. This achieves in particular protection against injuries on the cutting edge 11. In other words: exposure of the blade section 10 and the cutting edge 11 thereof during use on a patient and the components posing a risk of injury is prevented. Moreover, the first tube end 71 is guided in the radial direction between the leg section 12 and the first mating section 5 during insertion of the first mating section 5. This facilitates mating with the first medical tube line 7. The leg section 12 is to be considered advantageous, but not absolutely essential, with respect to the present invention. Accordingly, other embodiments do not have a leg section.

Further advantageous structural features and functional features of the tube connector 1 will be explained below. In different embodiments, these features are not necessarily present or are only present in part or are present in different combinations. With respect to the present invention, these features are, in this respect, not to be regarded as essential.

In the embodiment shown, the blade section 10 protrudes outwardly from the first mating section 5 in the radial direction RI of the first mating section 5 (FIG. 1). In the present case, the blade section 10 also has, in addition to the cutting edge 11, a first edge 101 and a second edge 102. The first edge 101 is flush with an outer contour 51 of the first mating section 5 that will be further described. The second edge 102 is flush with an outer contour 131 of a pipe section 13 of the body 2 that extends between the first mating section 5 and the second mating section 6. Other embodiments do not have a pipe section.

Furthermore, in the embodiment shown, the cutting edge 11 is elongate at an inclination relative to the first mating axis S1. As a consequence of the longitudinal inclination, the cutting edge 11 upon insertion of the first mating section 5 does not hit the first tube end 71 bluntly or abruptly over the entire length of said cutting edge 11. Instead, the cutting edge 11 cuts into the tube casing 72 gradually over the length of said cutting edge 11, and so said tube casing 72 is cut through along the radial direction RI from the inside to the outside and also axially.

The cutting edge 11 has a first edge end 111 and a second edge end 112. The first edge end 111 is positioned nearer to the first end 3 of the body 2 than the second edge end 112. The second edge end 112 is positioned nearer to the second end 4 of the body 2 than the first edge end 111. The cutting edge 11 rises from the first edge end 111 above the length of the first mating section 5 in the radial direction RI to the second edge end 112. In this respect, the second edge end 112 is positioned further outwardly in the radial direction RI than the first edge end 111.

In the embodiment shown, the cutting edge 11 is elongate in a continuously straight line between its first edge end 111 and the second edge end 112. In embodiments not depicted, the cutting edge can instead be curved, undulating, serrated or the like.

In the present case, the first edge end 111 is axially recessed by an axial distance A from the first end 3. The axial distance A extends parallel to the first longitudinal axis L1 and/or the first mating axis S1. In the embodiment shown, the axial distance A is approximately 50% of a total length of the first mating section 5 that is not further identified.

In a mated state, the outer contour 51 of the first mating section 5 interacts with an inner contour of the first tube end 71 that will be further identified. In the embodiment shown, the outer contour 51 is in the form the outer conical surface K1. In this respect, the outer contour 51 is cone-shaped, and so a cross-section of the first mating section 5 that is not further identified increases along the first mating axis 1 starting from the first end 3.

In the arrangement shown by means of FIGS. 2 and 3, the first medical tube line 7 is a catheter tube of a central venous catheter that is otherwise not further visible. The catheter tube has a first lumen 73 and a second lumen 74 that are separated from each other by means of a partition wall 75 in the longitudinal direction of the catheter tube. The two lumens 73, 74 each have an approximately semicircular cross-section. The first mating section 5 has a cross-section matched to the cross-section of the first lumen 73. Accordingly, in the present case, the cross-section of the first mating section 5 is likewise approximately semicircular. It is understood that the cross-section of the first mating section can be different in other embodiments.

The second mating section 6 has an inner contour 61 which, in a mated state, interacts with an outer contour 82 of the second tube end 81. In the embodiment shown, the inner contour 61 is in the form of an inner conical surface K2. Owing to the conical design, an inner diameter of the second mating section 6 that is not further identified decreases continuously along the second mating axis S2 starting from the second end 4.

In the arrangement shown by means of FIGS. 2 and 3, the second medical tube line 8 is a catheter supply line of said central venous catheter. The catheter supply line has a circular cross-section with an outer contour 82 shaped accordingly. The inner contour 61 is matched to the outer contour 82 dimensionally and in terms of its shape.

Furthermore, the first mating axis S1 and the second mating axis S2 in the tube connector 1 are elongate at an inclination to each other. In other words, the body 2 is angled at least once or cranked at least once. Accordingly, the connecting lumen 9 has a first lumen section 93 and a second lumen section 94. Proceeding from the first opening 91, the first lumen section 93 is elongate coaxially to the first mating axis S1 and thus also to the first longitudinal axis L1. Proceeding from the second opening 92, the second lumen section 94 is elongate coaxially to the second mating axis S2 and thus also to the second longitudinal axis L2.

In the present case, the body 2 is made of a plastics material M in one piece. Accordingly, in particular, the first mating section 5, the second mating section 6, the blade section 10 and the other sections are integrated into the body 2. In embodiments not further depicted in a drawing, at least one of said sections can be manufactured as a separate component and then joined together with the other sections of the tube connector.

Figure 4:
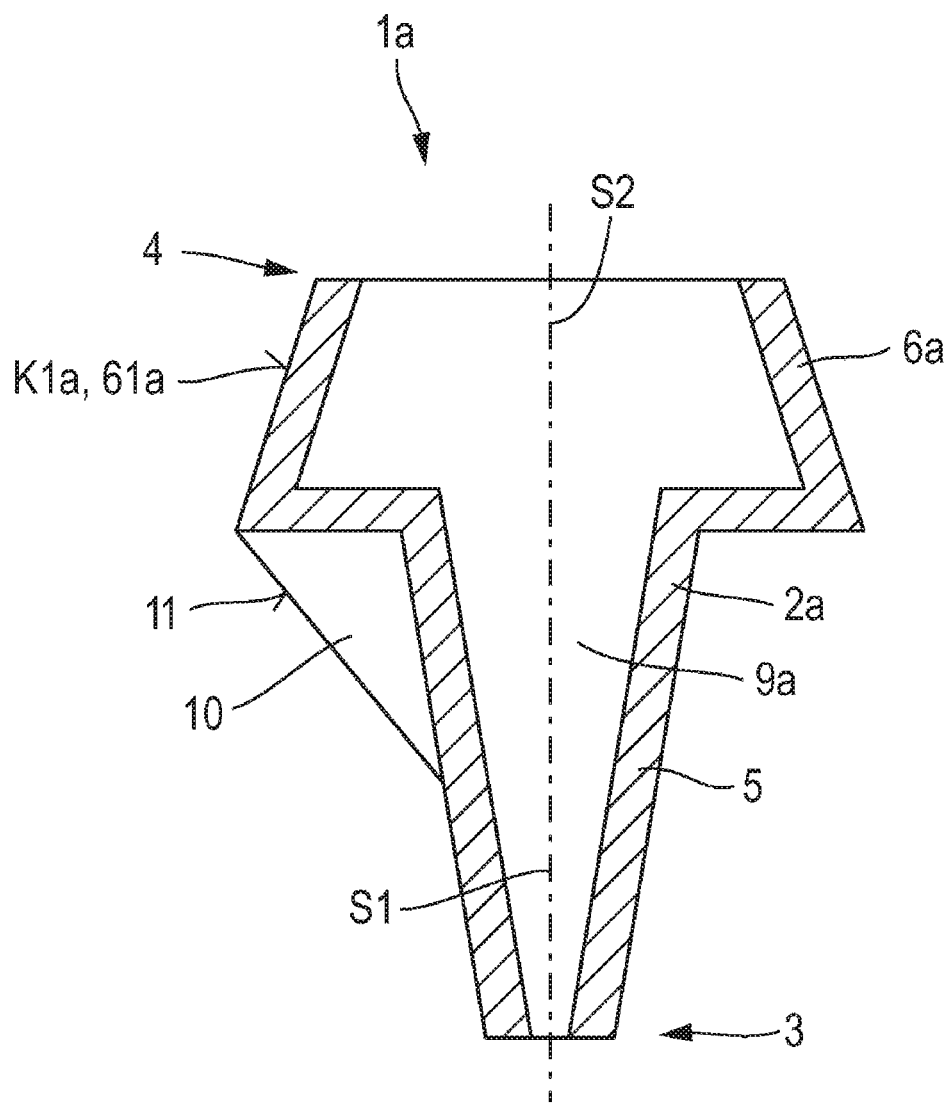
FIG. 4 shows a schematic longitudinal section of a further embodiment of a tube connector according to the invention.
Figure 5:
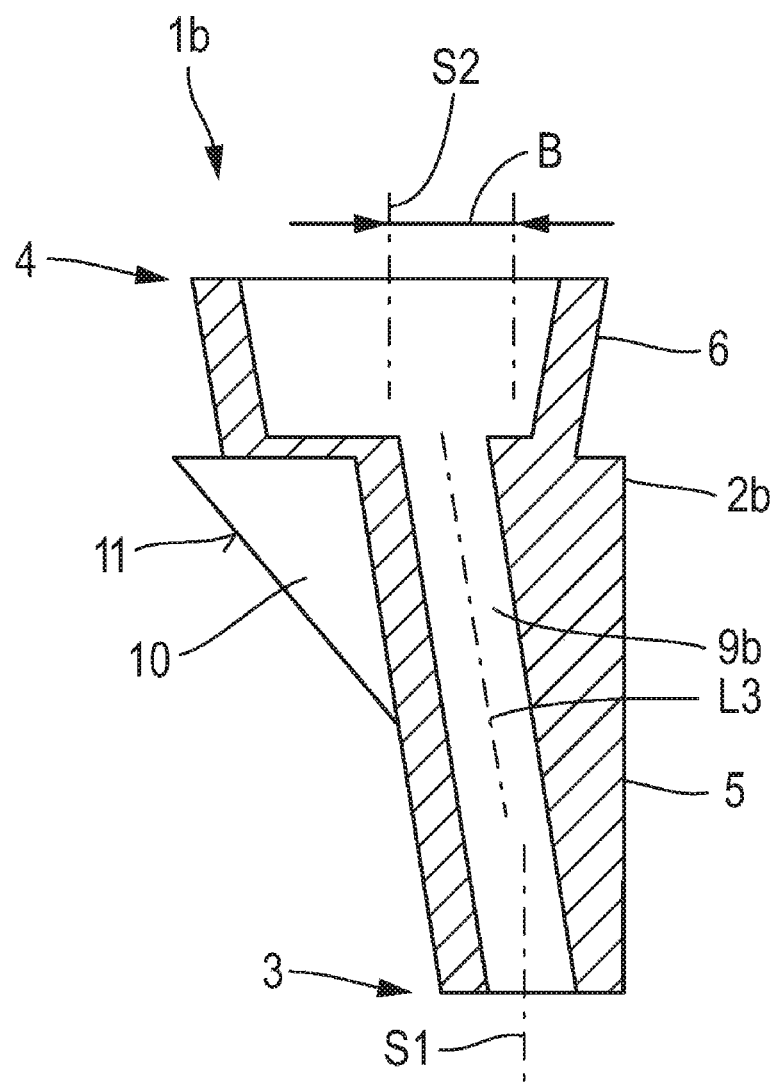
FIG. 5 shows a schematic longitudinal section of a further embodiment of a tube connector according to the invention.
Figure 6:
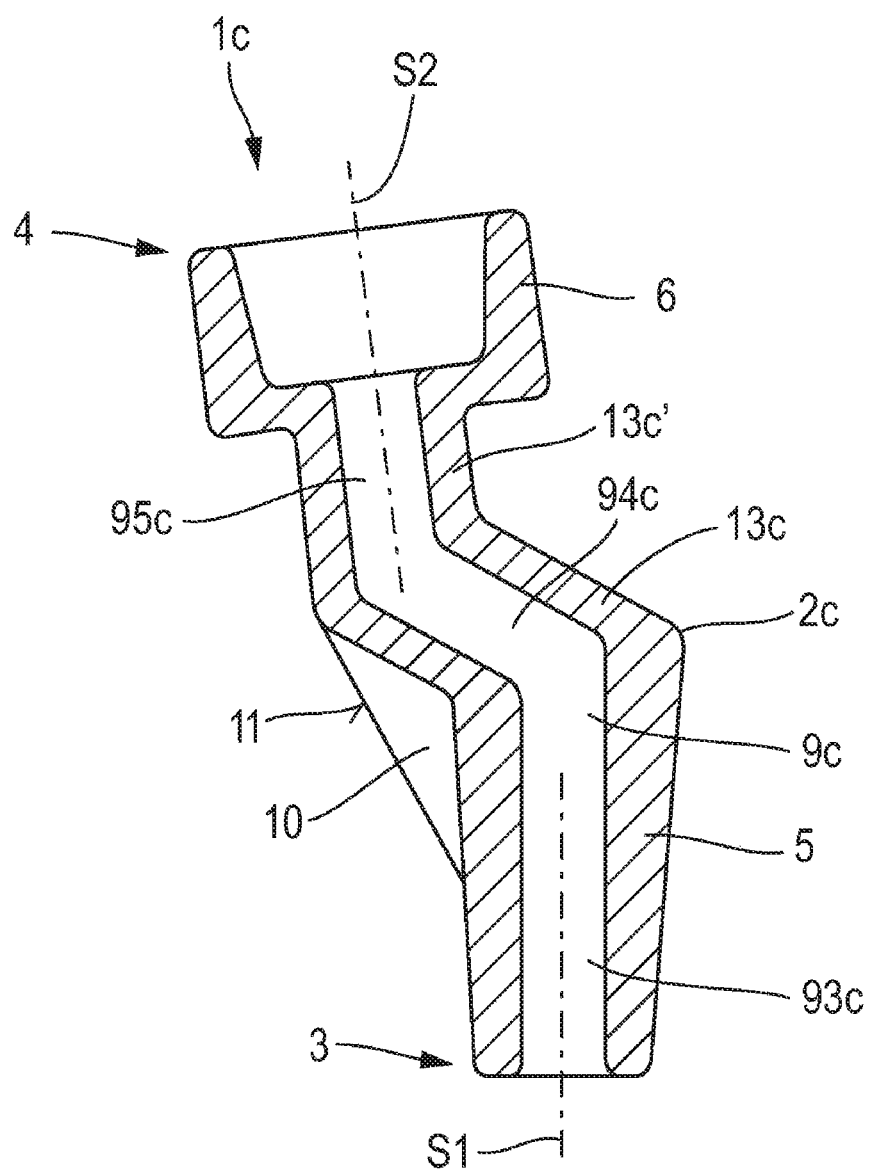
FIG. 6 shows a schematic longitudinal section of a further embodiment of a tube connector according to the invention.

FIGS. 4, 5 and 6 show further embodiments of tube connectors 1a, 1b, 1c according to the invention. The tube connectors 1a, 1b, 1c as per FIGS. 4 to 6 are substantially identical to the tube connector 1 as per FIGS. 1 to 3 with respect to their design and function. Therefore, to avoid repetition, only substantial differences will be discussed below. Apart from that, what has already been stated in relation to the tube connector 1 as per FIGS. 1 to 3 applies. Features which have an at least substantially identical design and function are provided with identical reference numerals. Additional or different features are identified by the addition of a lowercase reference letter.

The tube connector 1a as per FIG. 4 substantially differs from the tube connector 1 in the design of the second mating section 6a. The second mating section 6a is in the form of a male mating section and, in this respect, configured for insertion into a tube end to be connected. Accordingly, the second mating section 6a has an outer contour 61a which, in a mated state, interacts with an inner contour of the tube end to be connected. The outer contour 61a is in the form of the outer conical surface K1a.

Moreover, the body 2a of the tube connector 1a is elongate in a straight line, and so the first mating axis S1 and the second mating axis S2 are oriented coaxially to each other.

The tube connector 1b as per FIG. 5 substantially differs in that the first mating axis S1 and the second mating axis S2 are arranged axially offset by a radial distance B. In this case, the first mating axis S1 and the second mating axis S2 are parallel oriented. The connecting lumen 9b is oriented obliquely between the first end 3 and the second end 4 both in relation to the first mating axis S1 and in relation to the second mating axis S2. The connecting lumen 9b is elongate in a continuous straight line along its longitudinal axis L3, which can also be referred to as a lumen axis. Apart from that, the first mating section 5, the second mating section 6 and the blade section 10 do not have any substantial differences compared to the corresponding sections of the tube connector 1.

The tube connector 1c as per FIG. 6 differs from the tube connector 1 in a doubly angled design of the body 2c. Therefore, the body 2c has a doubly angled or cranked shape, i.e. is angled twice or cranked twice, and is provided with a pipe section 13c and a further pipe section 13c'. The pipe section 13c is referred to as first pipe section below. The pipe section 13c' is referred to as second pipe section below. The second pipe section 13c' is elongate parallel to the second mating axis S2. The first pipe section 13c is elongate at an inclination relative to the first mating axis S1 and the second mating axis S2, and one end thereof is connected to the second pipe section 13c' and the other end thereof is connected to the first mating section 5. The connecting lumen 9c is elongate between the first end 3 and the second end 4 of the body 2c and has a first lumen section 93c, a second lumen section 94c and a third lumen section 95c. The first lumen section 93c is elongate coaxially through the first mating section 5. The second lumen section 94c is elongate coaxially through the first pipe section 93c. The third lumen section 95c is elongate coaxially through the second pipe section 13c'.

Figure 7:
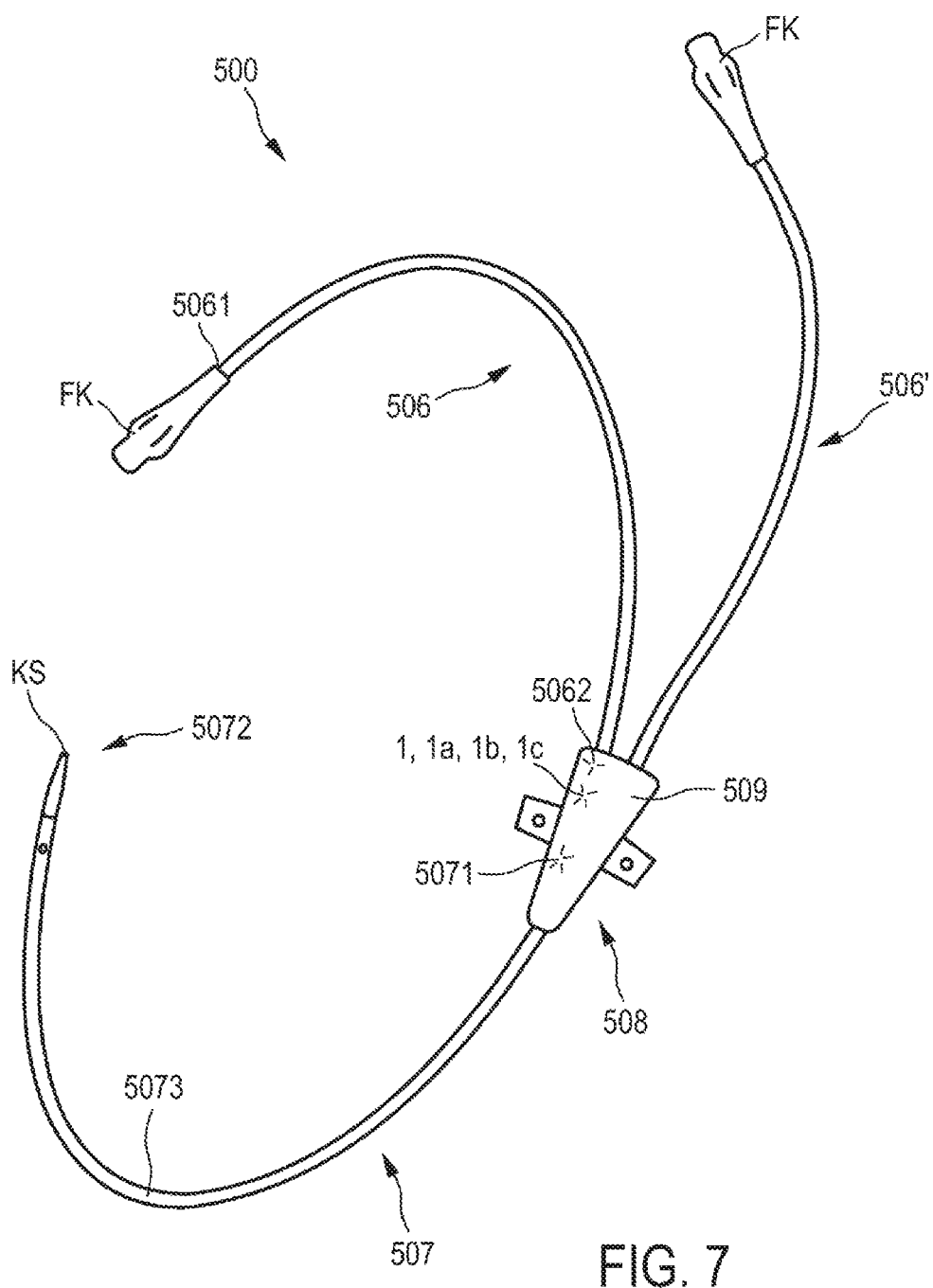
FIG. 7 shows a schematic perspective view of one embodiment of a catheter arrangement according to the invention.

FIG. 7 shows one embodiment of a catheter arrangement 500 according to the invention. The catheter arrangement 500 is provided in the form of a central venous catheter for use in infusion therapy. The catheter arrangement 500 comprises at least one catheter supply line 506, a catheter tube 507 and at least one tube connector 1, 1a, 1b, 1c according to the preceding embodiments.

The catheter supply line 506 acts as first medical tube line. The catheter tube 507 acts as second medical tube line. According to what has been described above, the tube connector 1, 1a, 1b, 1c is mated, firstly, with the first medical tube line, i.e., the catheter supply line 506, and, secondly, with the second medical tube line, i.e., the catheter tube 507. In this respect, to avoid repetition, reference is made to what has been described above.

The catheter supply line 506 is elongate between a proximal end 5061 and a distal end 5062. The catheter tube is elongate between a proximal end 5071 and a distal end 5072. The distal end 5072 forms a catheter tip KS of the catheter arrangement 500. The tube connector 1, 1a, 1b, 1c establishes a fluid connection between the distal end 5062 of the catheter supply line 506 and the proximal end 5071 of the catheter tube 507.

To produce the catheter arrangement 500, the tube connector 1, 1a, 1b, 1c, more precisely the first mating section thereof, is mated with the proximal end 5071 of the catheter tube 507. Here, the cutting edge cuts through the tube casing 5073 of the catheter tube 507 in the axial direction, and so the tube connector 1, 1a, 1b, 1c can be advanced along the catheter tube 507 to a desired position. A section of the tube casing that is subsequently proximally protruding (axially cut through) is cut off or removed in some other way. Thereafter, the second mating section of the tube connector 1, 1a, 1b, 1c is mated with the distal end 5062 of the catheter supply line 506.

In this context, the tube connector 1, 1a, 1b, 1c primarily acts as an assembly aid for (pre)connection of the catheter tube 507 to the catheter supply line 506.

In the present case, an actual joint between the catheter tube 507 and the catheter supply line 506 is brought about by means of a fixing section 508. In the embodiment shown, the fixing section 508 is a plastics overmold 509. In the present case, the plastics overmold 509 completely sheaths the tube connector 1, 1a, 1b, 1c, and so said tube connector 1, 1a, 1b, 1c is accordingly covered in FIG. 7 and cannot be seen in detail.

In the present case, the catheter arrangement 500 also comprises a further catheter supply line 506'. The catheter supply line 506' can be connected to the catheter tube by means of a further tube connector. In particular, in the present case, the catheter supply line 506 is fluidically connected to a first lumen of the catheter tube 507 and the further catheter supply line 506' is connected to a second lumen of the catheter tube 507.

Apart from that, the catheter supply line 506 and the further catheter supply line 506' both have a fluid connector FK for fluid connection to further fluid components.

The invention claimed is:
1. A tube connector for medical tube lines, the tube connector comprising:
  a body having a first end and a second end;
  a first mating section arranged at the first end and configured for axial insertion into a first tube end of a first medical tube line along a first mating axis;
  a second mating section arranged at the second end and configured for axial mating with a second tube end of a second medical tube line along a second mating axis; and
  a connecting lumen which is elongate between the first end and the second end through the body, the connecting lumen forming a fluid connection between a first opening in the first mating section and a second opening in the second mating section, the body comprising at least one blade section which is assigned to the first mating section and a cutting edge oriented in a direction of the first mating axis, and the first tube end of the first medical tube line being axially slitable by the cutting edge upon insertion of the first mating section, wherein the cutting edge has a first edge end positioned nearer to the first end and a second edge end positioned nearer to the second end, the first edge end being recessed axially in a direction of the second end by an axial distance along the first mating axis relative to an end face of the first mating section.

2. The tube connector according to claim 1, wherein the cutting edge is configured for cutting through a tube casing of the first medical tube line, so that the tube connector, when the first mating section is inserted into the first medical tube line, is positionable along the first medical tube line while the cutting edge cuts through the tube casing.

3. The tube connector according to claim 1, wherein the at least one blade section protrudes outwardly from the first mating section in a radial direction.

4. The tube connector according to claim 1, wherein the cutting edge is elongate at an inclination relative to the first mating axis.

5. The tube connector according to claim 1, wherein the axial distance is between 30% and 70% of a total length of the first mating section.

6. The tube connector according to claim 1, wherein the first edge end is flush with an outer contour of the first mating section, and wherein the second edge end is flush with an outer contour of the second mating section.

7. The tube connector according to claim 1, wherein the first mating section has a first outer conical surface and/or wherein the second mating section has a second outer conical surface or an inner conical surface.

8. The tube connector according to claim 1, wherein the first mating axis and the second mating axis are oriented parallel to one another and radially spaced by a radial distance.

9. The tube connector according to claim 8, wherein the connecting lumen is oblique relative to the first mating axis and the second mating axis, and wherein the connecting lumen is elongate in a continuous straight line along a lumen axis.

10. The tube connector according to claim 1, wherein the first mating axis and the second mating axis are elongate at an inclination to each other.

11. The tube connector according to claim 10, wherein the connecting lumen is angled at least once, such that a first section of the connecting lumen is elongate coaxially to the first mating axis and a second section of the connecting lumen is elongate coaxially to the second mating axis.

12. The tube connector according to claim 1, wherein the body is made of a plastics material in one piece.

13. A catheter arrangement comprising:
a tube connector according to claim 1;
at least one catheter supply line; and
a catheter tube,
wherein the at least one catheter supply line and the catheter tube are connected to each other by the tube connector, and
wherein a fixing section fixes the connection between the at least one catheter supply line and the catheter tube.

14. The catheter arrangement according to claim 13, wherein the fixing section is formed by a plastics overmold, the plastics overmold completely sheathing the tube connector.

15. A tube connector for medical tube lines, the tube connector comprising:
a body having a first end and a second end;
a first mating section arranged at the first end and configured for axial insertion into a first tube end of a first medical tube line along a first mating axis;
a second mating section arranged at the second end and configured for axial mating with a second tube end of a second medical tube line along a second mating axis; and
a connecting lumen which is elongate between the first end and the second end through the body,
the connecting lumen forming a fluid connection between a first opening in the first mating section and a second opening in the second mating section,
the body comprising at least one blade section which is assigned to the first mating section and a cutting edge oriented in a direction of the first mating axis, and
the first tube end of the first medical tube line being axially slitable by the cutting edge upon insertion of the first mating section,
wherein the body is made of a plastics material in one piece.

16. A catheter arrangement comprising:
a first catheter tube;
a second catheter tube;
a tube connector comprising:
a body having a first end and a second end,
a first mating section arranged at the first end and configured for axial insertion into the first catheter tube along a first mating axis,
a second mating section arranged at the second end and configured for axial mating with the second catheter tube along a second mating axis, and
a connecting lumen which is elongate between the first end and the second end through the body,
the connecting lumen forming a fluid connection between the first catheter tube and the second catheter tube,
the body comprising at least one blade section which is assigned to the first mating section and a cutting edge oriented in a direction of the first mating axis, and
a tube end of the first catheter tube being axially slitable by the cutting edge upon insertion of the first mating section into the first catheter tube; and
a fixing section fixing the connection between the first catheter tube and the second catheter tube.

* * * * *